(12) United States Patent
Jantzen et al.

(10) Patent No.: US 8,337,542 B2
(45) Date of Patent: Dec. 25, 2012

(54) DELIVERY SYSTEM FOR SIMULTANEOUS DEPLOYMENT OF INTRALUMINAL DEVICE

(75) Inventors: Alexandra Elizabeth Jantzen, Durham, NC (US); Nathaniel A. Irwin, Bloomington, IN (US); Thomas W. McGhie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 244 days.

(21) Appl. No.: 12/836,297

(22) Filed: Jul. 14, 2010

(65) Prior Publication Data

US 2012/0016454 A1    Jan. 19, 2012

(51) Int. Cl.
*A61F 2/06* (2006.01)

(52) U.S. Cl. ............... 623/1.11; 623/1.12; 623/1.35; 606/108; 604/284

(58) Field of Classification Search ............. 604/284
See application file for complete search history.

(56) References Cited

U.S. PATENT DOCUMENTS

| | | | |
|---|---|---|---|
| 5,507,769 A | 4/1996 | Marin et al. | |
| 5,669,924 A | 9/1997 | Shaknovich | |
| 5,720,735 A | 2/1998 | Dorros | |
| 6,099,497 A | 8/2000 | Adams et al. | |
| 6,143,002 A | 11/2000 | Vietmeier | |
| 6,261,273 B1 | 7/2001 | Ruiz | |
| 6,368,345 B1 | 4/2002 | Dehdashtian et al. | |
| 6,482,211 B1 | 11/2002 | Choi | |
| 6,514,281 B1 | 2/2003 | Blaeser et al. | |
| 6,884,258 B2 | 4/2005 | Vardi et al. | |
| 6,908,477 B2 | 6/2005 | McGuckin, Jr. et al. | |
| 7,402,141 B2 | 7/2008 | Heuser | |
| 7,481,837 B2 | 1/2009 | Wilson | |
| 2005/0125050 A1* | 6/2005 | Carter et al. ............ | 623/1.11 |
| 2009/0012601 A1 | 1/2009 | Siu et al. | |

* cited by examiner

*Primary Examiner* — Bruce E Snow
*Assistant Examiner* — Brian Dukert
(74) *Attorney, Agent, or Firm* — Brinks Hofer Gilson & Lione

(57) ABSTRACT

A medical device delivery system includes a retention sheath having a proximal portion and a bi-furcated distal portion having first and second sheath branch portions. The proximal ends of the sheath branch portions are joined together at a sheath branch junction. The system also includes an inner catheter disposed within the retention sheath. The inner catheter includes a proximal portion and a bi-furcated distal portion with first and second catheter branch portions. The proximal ends are joined together at a catheter branch junction. When the sheath is in an initial position, the catheter branch junction is displaced proximally from the sheath branch junction by a distance that is greater than or equal to the larger of a length of a first medical device and the length of a second medical device.

6 Claims, 17 Drawing Sheets

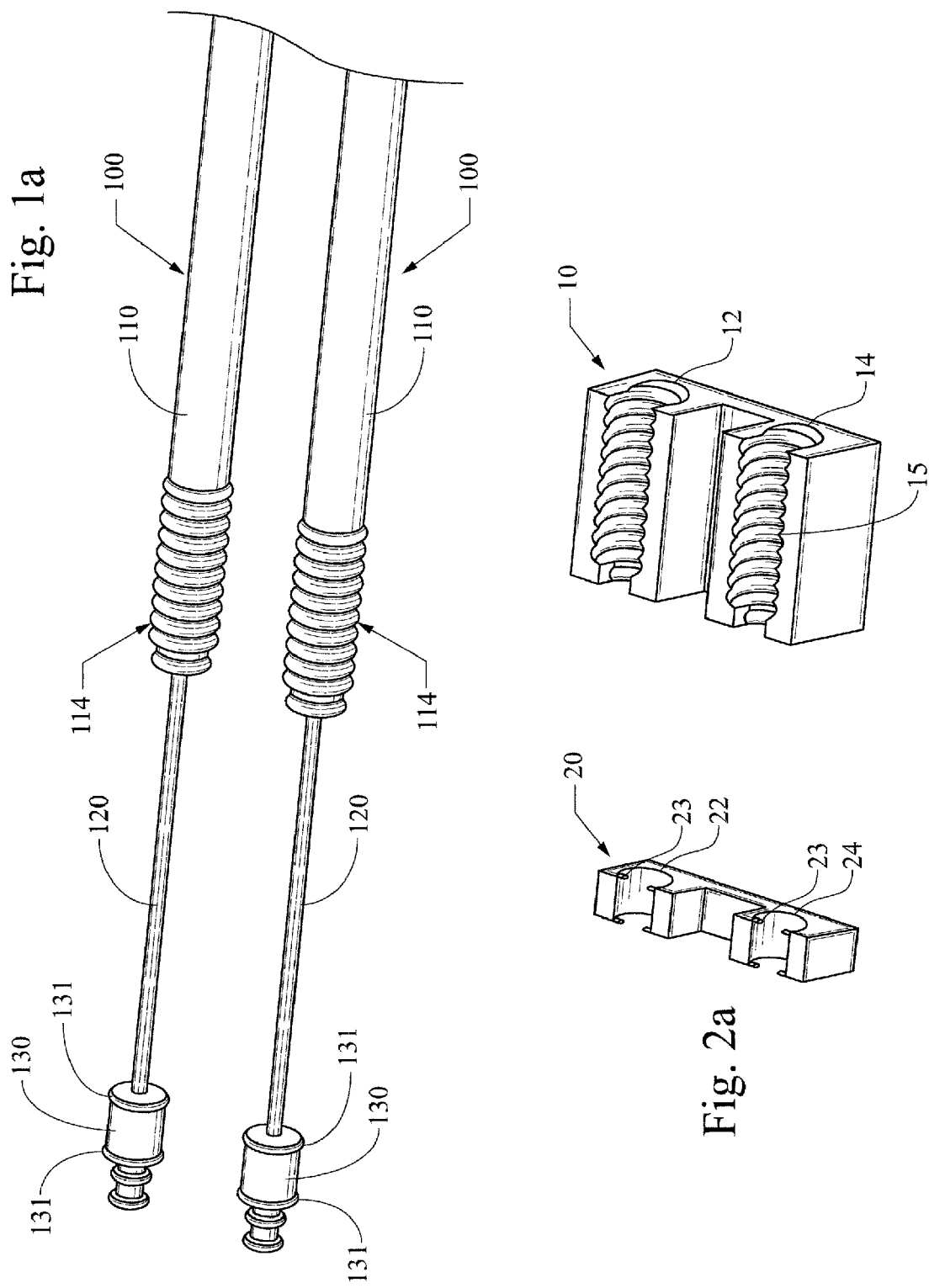

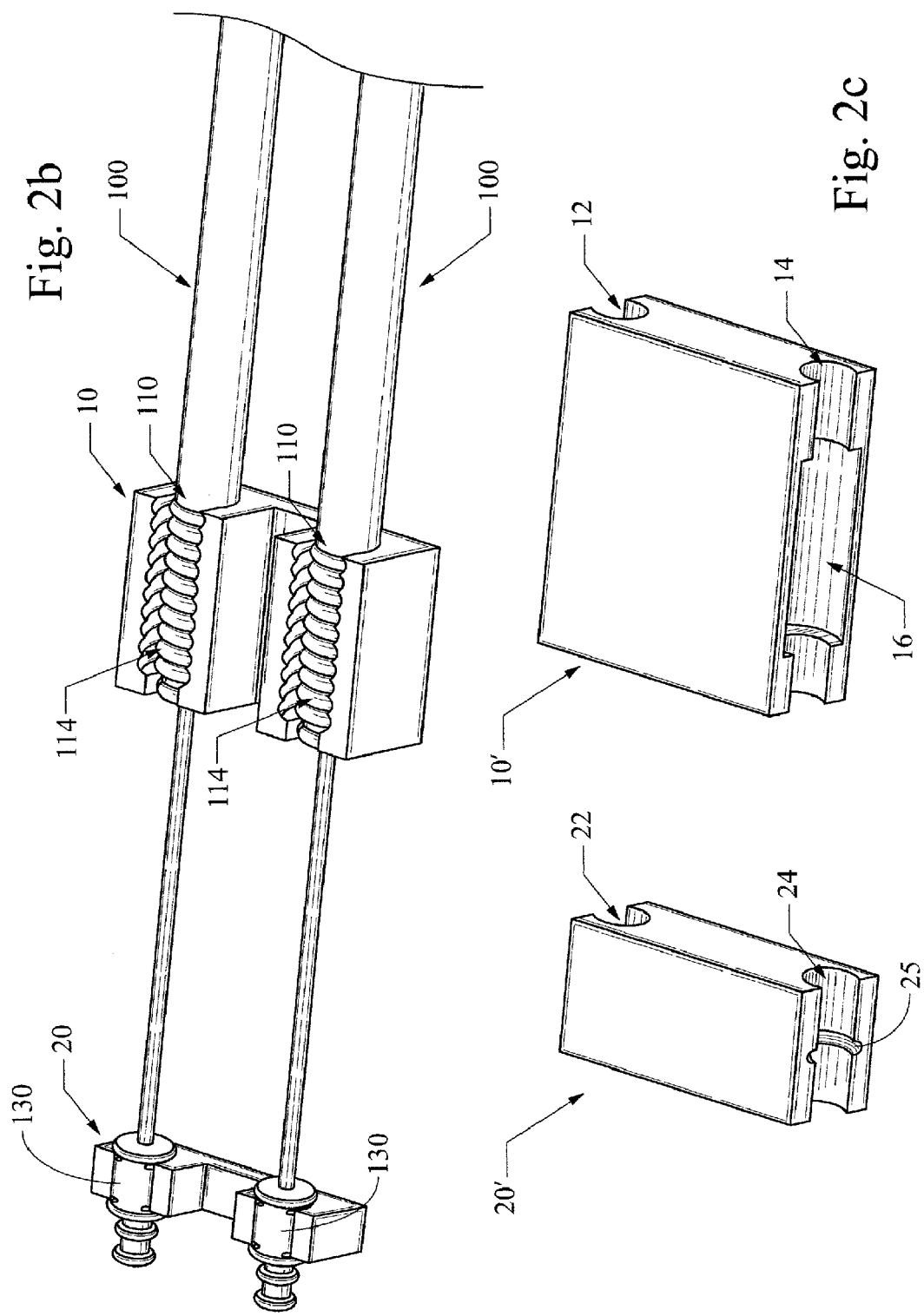

DELIVERY SYSTEM FOR SIMULTANEOUS DEPLOYMENT OF INTRALUMINAL DEVICE

BACKGROUND

The present invention relates generally to medical devices and more particularly to delivery systems for deploying implantable intraluminal devices in a bifurcated vessel or the like.

Stents have become a common alternative for treating vascular conditions, such as stenoses or the like, because stenting procedures are considerably less invasive than other alternatives. Stenoses can cause blood vessels and other body lumens or cavities to become narrowed or occluded by lesions or the like. These lesions may restrict or in some cases block the flow of blood or other bodily fluids through the affected vessel.

One area in which stenotic lesions commonly form is at a point of bifurcation within a blood vessel in which a single vessel, for example, the iliac artery, branches into two or more branch vessels. In such cases, the lesion(s) may affect a single vessel, or two or more of the vessels connected by the bifurcation. One method of treating such lesions is the so-called "kissing stent" technique in which two stents are deployed simultaneously such that one portion of each stent is disposed in each of the affected branch vessels and another portion is disposed in the single, main vessel to reconstruct the bifurcation. Upon deployment, a portion of the stents disposed in the main vessel come into contact with and expand against each other, hence the term "kissing stents." In the case of, for example, iliac artery lesions, the stents are commonly deployed using a dual femoral approach in which two separate delivery systems are inserted into the femoral arteries, one in each leg, advanced to the bifurcation, and deployed simultaneously to form the "kissing stent" configuration. In the event that the two stents are not deployed at substantially the same time, the stents may fail to contact each other and support the vessel wall, and in extreme cases, may obstruct the flow of blood and cause thrombi to form.

SUMMARY

Embodiments of medical device delivery systems are described, which may allow for simultaneous deployment of medical devices within a body vessel or cavity. The invention may include any of the following aspects in various combinations and may also include any other aspect described below in the written description or in the attached drawings.

In one aspect, a connector system for two discreet medical device delivery systems may include a first connector that is shaped to engage and connect a first portion of a first medical device delivery system to a first portion of a second medical device delivery system. The first and second medical device delivery systems may each include an inner catheter disposed within a retention sheath, and the first portions of the first and second delivery systems may be attached to a proximal portion of the inner catheter. The system also includes a second connector that is shaped to engage and connect a second portion of the first medical device delivery system to a second portion of the second medical device delivery system. The second portions of the first and second medical device delivery systems may be attached to a proximal portion of the retention sheaths. When one of the second portions is moved relative to the first portions, the first and second connectors cause the retention sheaths to move simultaneously relative to the inner catheters between a restraining position, in which each of the retaining sheaths cover and restrain a medical device disposed therein, and a deployment position, in which the retaining sheaths are removed from and release the medical devices, whereby the medical devices are deployed simultaneously.

In another aspect, a medical device delivery system may include a retention sheath having a proximal portion and a bi-furcated distal portion. The bi-furcated distal portion includes first and second sheath branch portions having proximal and distal ends. The proximal ends of the sheath branch portions are joined together at a sheath branch junction. An inner catheter may be disposed within the retention sheath. The inner catheter includes a proximal portion disposed within the proximal portion of the sheath and a bi-furcated distal portion including first and second catheter branch portions. The catheter branch portions have proximal ends that are joined together at a catheter branch junction. A first medical device having a first length is disposed within the first sheath branch portion, and a second medical device having a second length is disposed within the second sheath branch portion. When the retention sheath is in an initial position, the catheter branch junction is displaced proximally from the sheath branch junction by a distance that is greater than or equal to the larger of the first length of the first medical device and the second length of the second medical device.

In another aspect, the first and second medical devices and stents may have the same length. The retention sheath may be movable between the initial position in which the retention sheath is disposed over and restrains the stents, and a deployment position in which the retention sheath is withdrawn proximally to release the stents simultaneously.

In yet another aspect, a medical device delivery system may include an outer sheath connected to a first portion of a handle; first and second inner catheters attached to a second portion of the handle; a first retention sheath disposed around the first inner catheter and connected to a third portion of the handle; a second retention sheath disposed around the second inner catheter and connected to the third portion of the handle; a first medical device disposed around the first inner catheter and within the first retention sheath; and a second medical device disposed around the second inner catheter and within the second retention sheath. The first and second retention sheaths may be slidably disposed within a central lumen of the outer sheath, and the third portion of the handle may be movable relative to the first and second portions of the handle between a first position, in which the first and second retention sheaths are disposed around and restrain the first and second medical devices, respectively, and a second position in which the first and second retention sheaths are withdrawn proximally to deploy the first and second medical devices. The first and second medical devices are deployed simultaneously when the third portion of the handle is moved to the second position.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

The invention may be more fully understood by reading the following description in conjunction with the drawings, in which:

FIG. 1a is perspective view of two of the medical device deployment systems shown in FIG. 1;

FIGS. 2(a) and (c) illustrate embodiments of connector systems;

FIG. 2(b) is a perspective view of the connector system of FIG. 2a attached to the delivery systems of FIG. 1a;

DETAILED DESCRIPTION

Referring now to the figures, FIGS. 1-1(a) and 2(a)-(c) illustrate delivery systems 100 for a self-expanding stent, such as the Zilver® introducer produced by Cook Inc., the assignee of the present application. The delivery system includes a retention sheath 140, a control device 101, an inner catheter 144, and a medical device, for example, a balloon expandable or self-expanding stent (shown in FIGS. 6 and 7). The medical device is disposed in a device containing region within the inner catheter 144 and the retention sheath 140.

Figure 6:
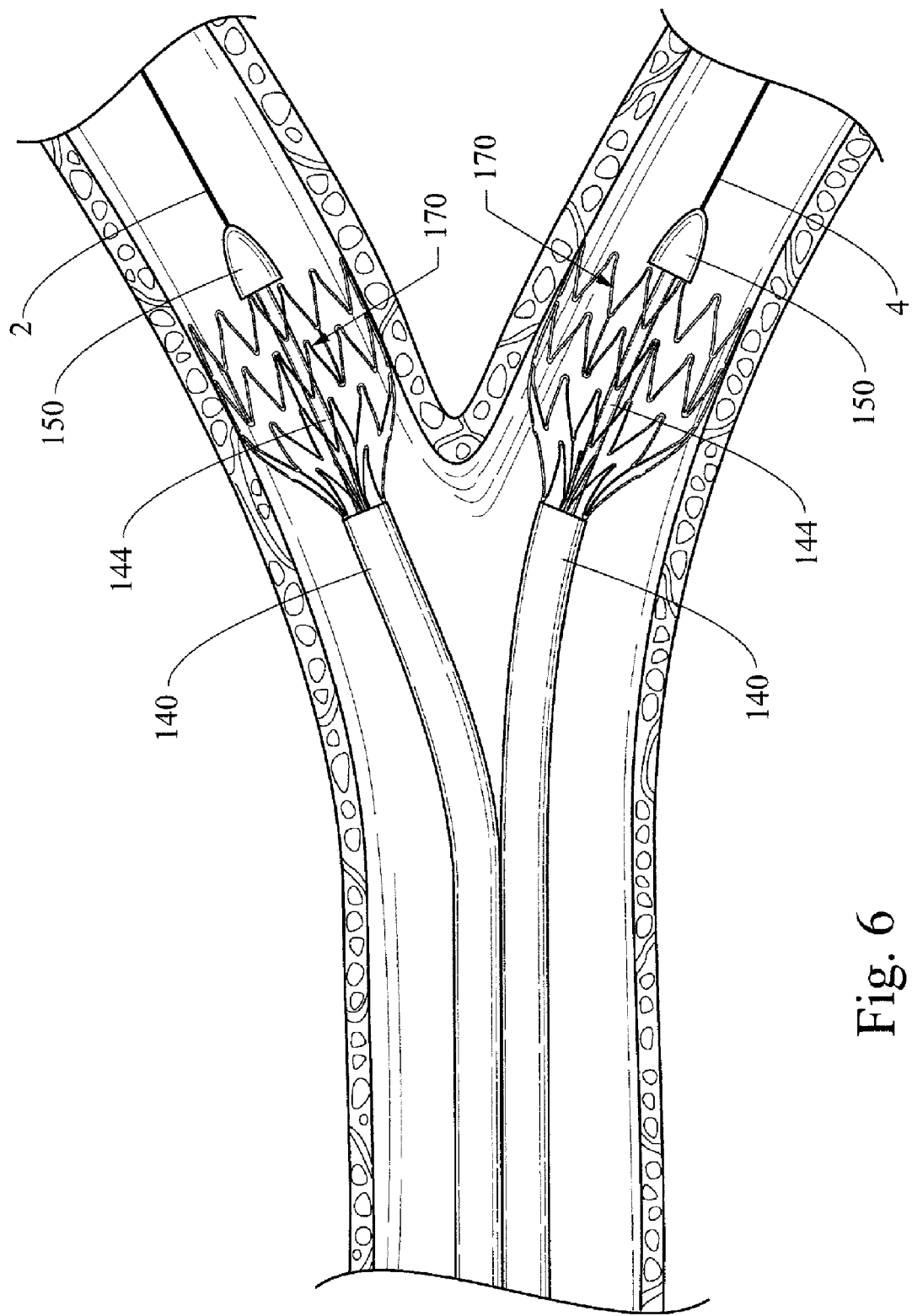
Figure 7:
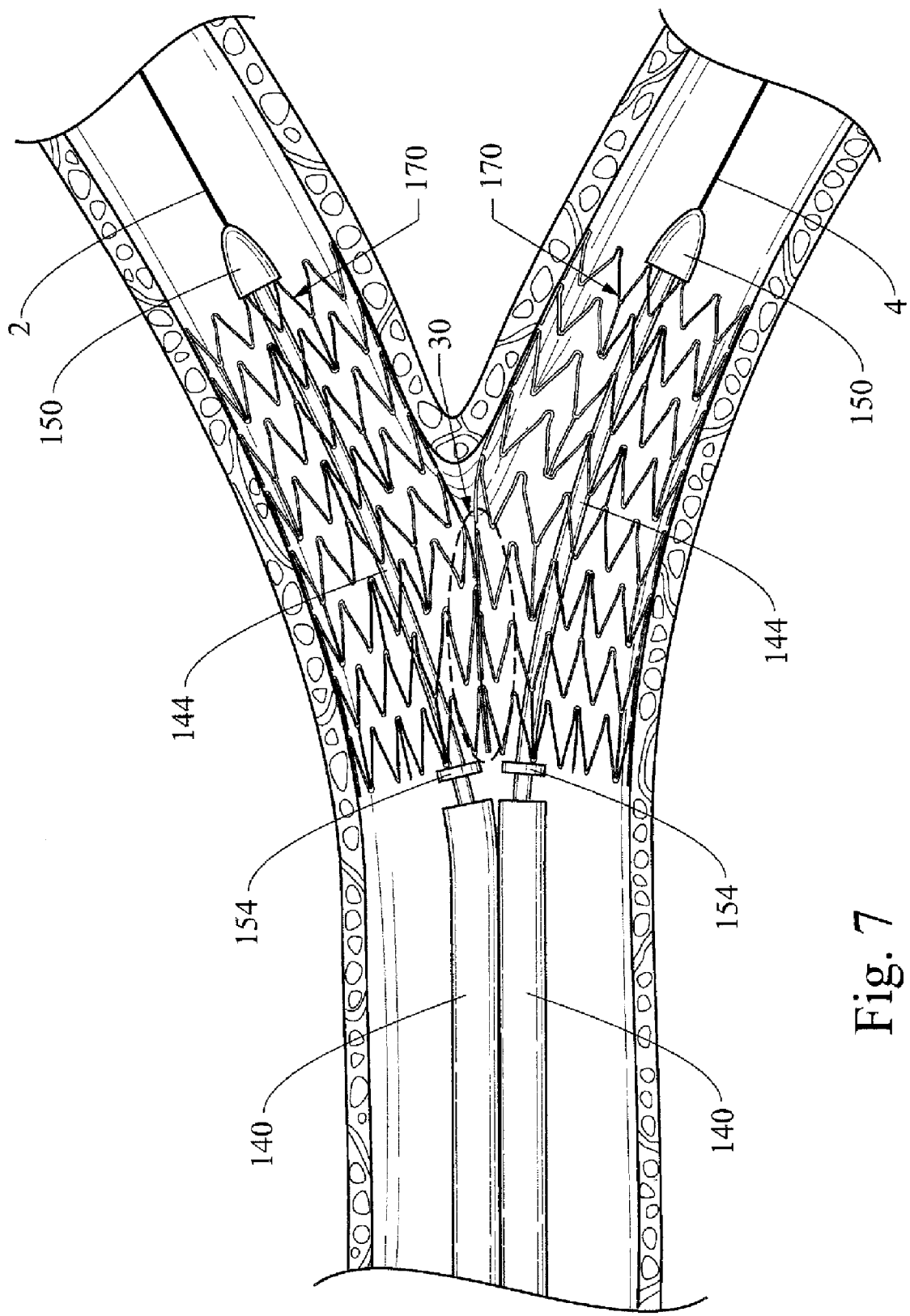

As is well understood by those skilled in the art, the medical device is initially mounted within the retention sheath 140 at the distal end of the inner catheter 144. As shown in FIGS. 6 and 7, the medical device may be a self-expanding stent made from a framework of braided wire filaments, or may have a plurality of serpentine rings interconnected with longitudinal struts. Other well-known stent structures are also possible. Various materials may be used for the self-expanding stent 110, such as nitinol or stainless steel. The stent may also be balloon expandable, in which case the inner catheter 144 may also include a balloon disposed in the device containing region, or a separate balloon catheter may be disposed within the retention sheath 140.

The inner catheter 144 may include a stop 154 that extends radially outward from the inner catheter 144 and a distal tip 150 that may be bonded to the distal end of the inner catheter 144 using an adhesive or the like. As shown in FIGS. 6 and 7, a distal surface of the stop 154 is located adjacent a proximal end of the stent 170. The stent 170 may be released from the delivery system by withdrawing the retention sheath 140 proximally relative to the inner catheter 144. During deployment, when the proximal end of the stent 170 contacts the distal end of the stop 154, the stop 154 prevents the stent 170 from continuing to move proximally, thereby separating the stent 170 from the retention sheath 140.

Figure 1:
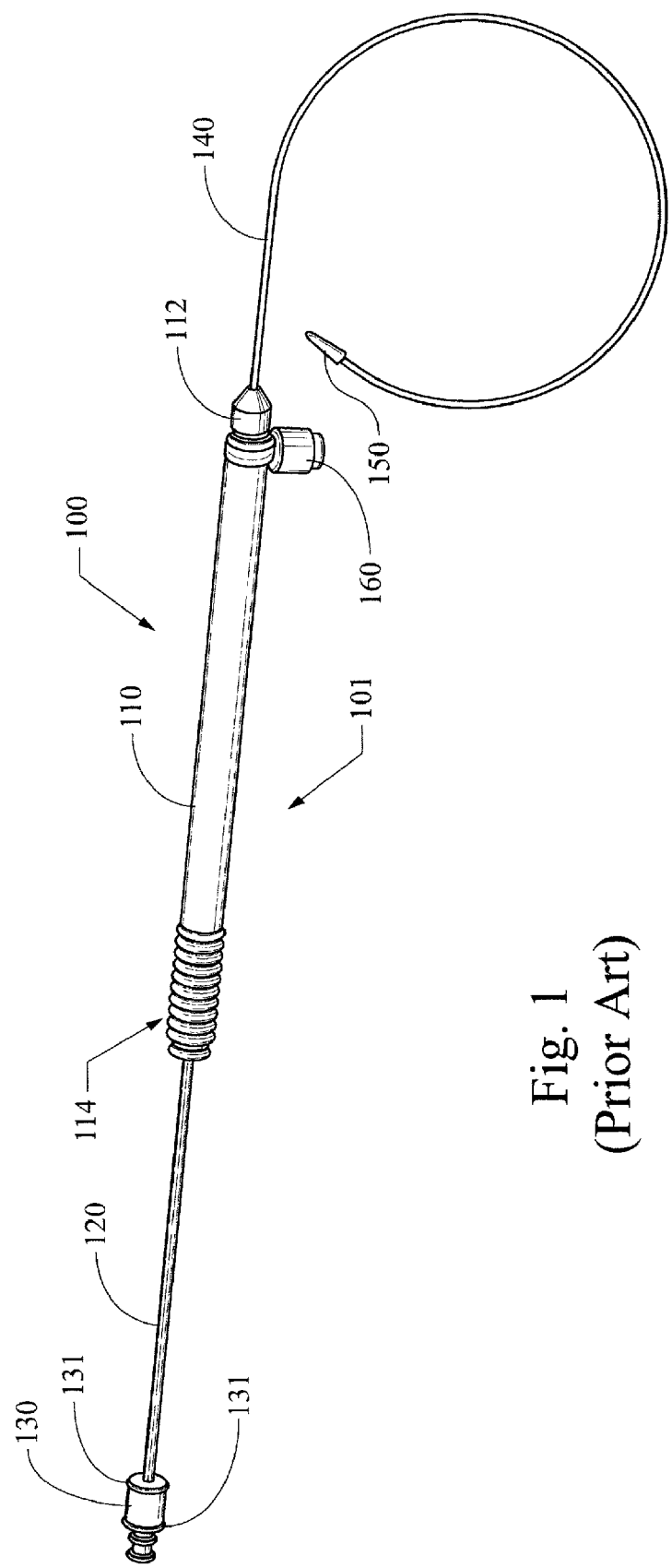
FIG. 1 is a perspective view of a conventional medical device deployment system.
Figure 3:
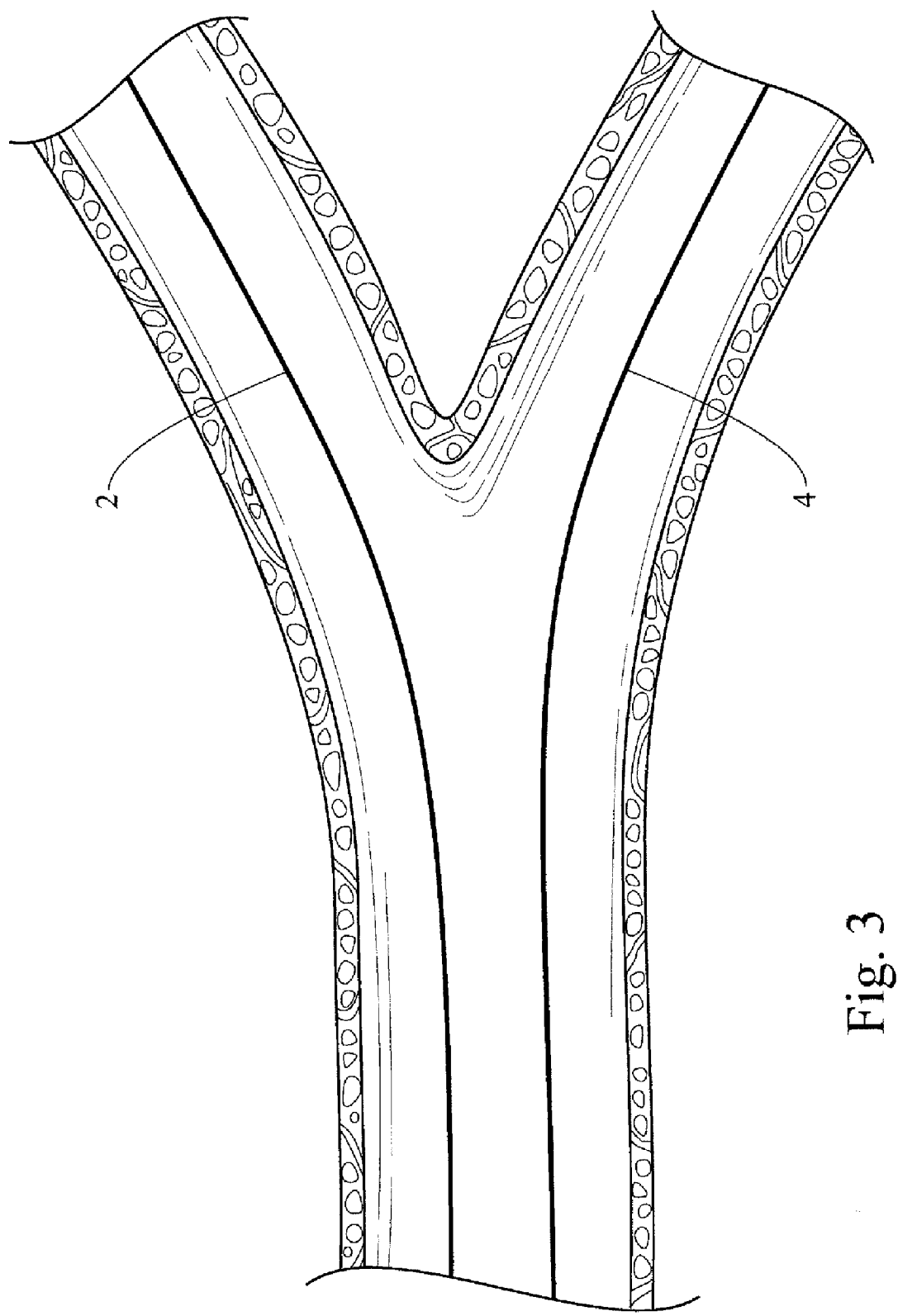
FIGS. 3-7 illustrate a deployment process for the medical devices housed within the connected delivery systems of FIG. 2(b)
Figure 4:
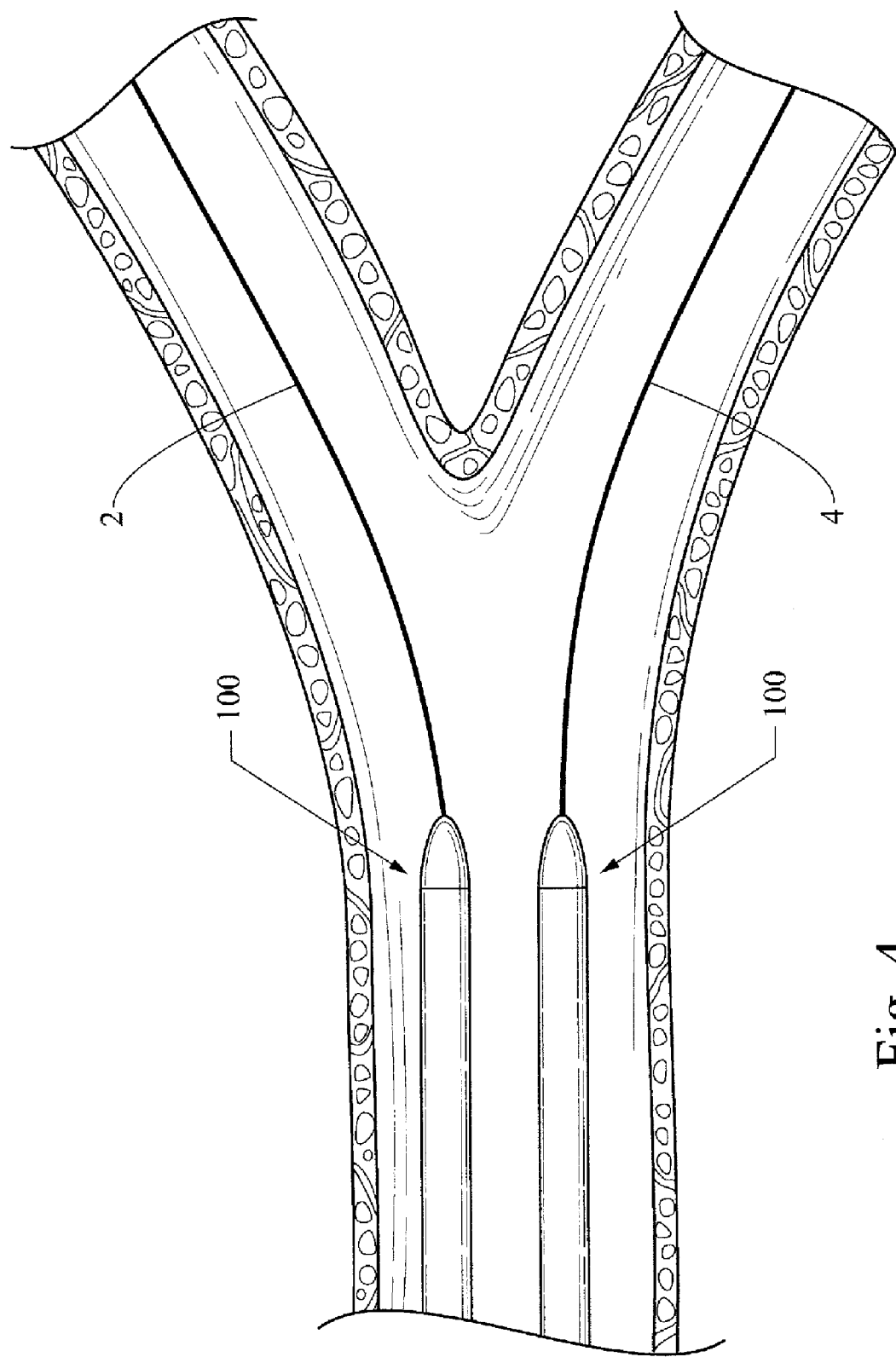
Figure 5:
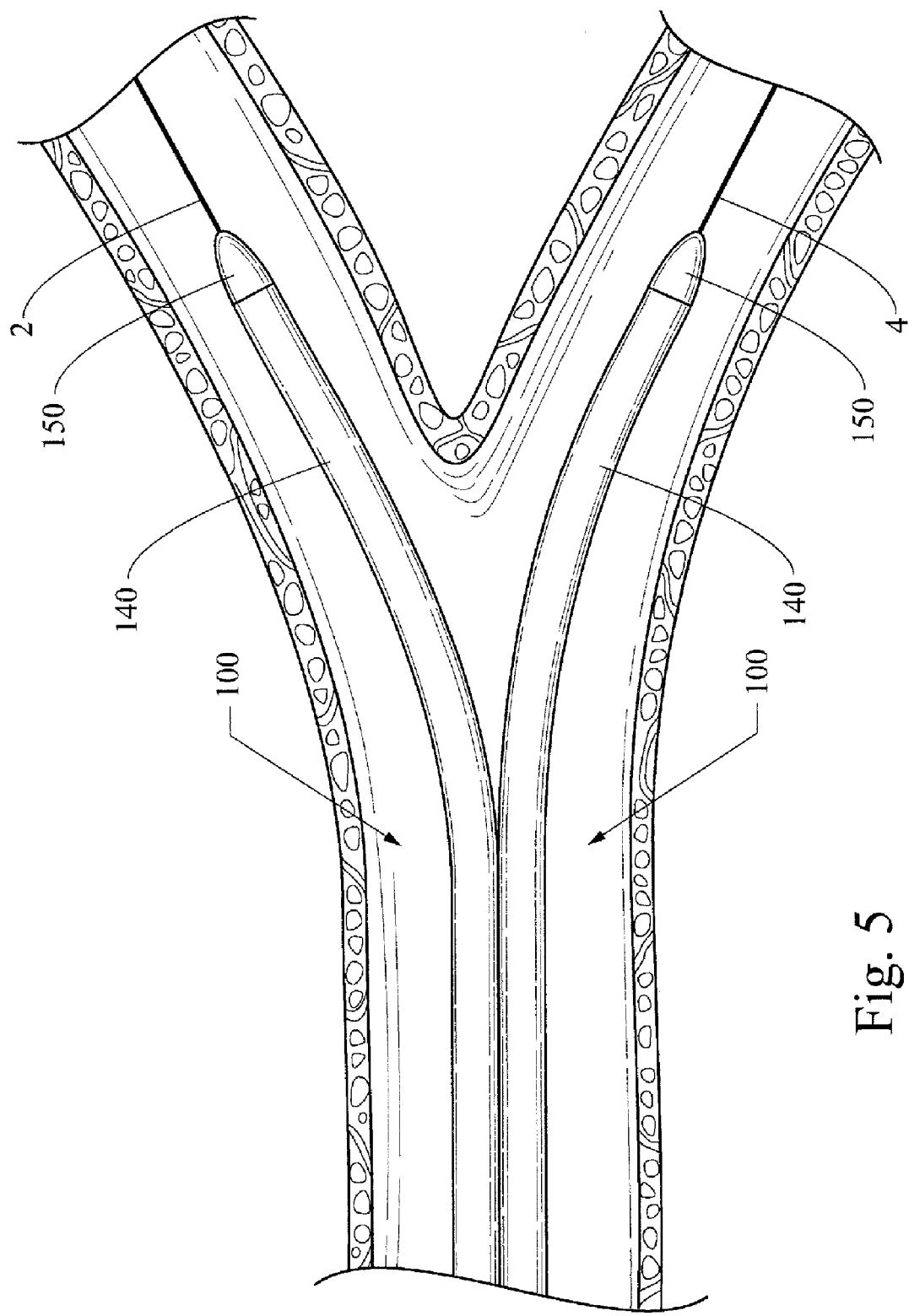

The delivery system 100 also includes a control device 101, which may be used to deploy the stent 170, is shown in FIGS. 6-7. FIG. 1 shows the control device 101 in an initial position before the stent 170 is deployed. The control device 101 may include a proximal control knob 130. The control device 101 may also include handle 110 displaced distally from the control knob 130. The control knob 130 may be attached to a shaft 120 that extends through the handle 110. The proximal end of the inner catheter 144 may be connected to the shaft 120 in a sandwiched configuration by the control knob 130. The handle 110 is attached to the retention sheath 140. If desired, a guide wire lumen may pass through the shaft 120 and the control knob 130 to allow one or more guide wires 2, 4 (see FIGS. 3-7) to pass through the inner catheter 144, the control device 101, and out the proximal end of the control knob 130. A port 160 may also be provided on the handle 110 to pass fluids, for example, contrast fluid, through the delivery system to the treatment site.

FIGS. 2(a) and (c) illustrate embodiments of a connector system for connecting two separate, distinct delivery systems 100 together to allow for fail-safe simultaneous deployment of the stents 170. As shown in FIG. 2(a), the connector system may include a first connector 10 and a second connector 20. The first connector includes first and second attachment portions 12, 14 having vertically extending wall members that are shaped to interface with and engage an external surface of the handles 110 of the delivery systems 100. Similarly, the second connector 20 includes first and second attachment portions 22, 24 having vertically extending wall members that are shaped to interface with and engage an external surface of the control knobs 130 of the delivery devices 100.

In one embodiment, the wall members of the attachment portions 12, 14 may be configured to extend around more than 50% of the external surface of the handle 110 at a selected longitudinal attachment position. Likewise the wall members of the attachment portions 22, 24 of the second connector 20 are configured to extend around more than 50% of the external surface of the control knobs 130 at a selected longitudinal attachment position. In this way, the connectors 10, 20 can be attached in a detachable snap-fit manner that allows the connectors 10, 20 to, 1) be readily attached to the delivery systems 100 for simultaneous deployment of the medical devices, and 2) be readily detached after deployment for reuse in subsequent procedures. However, it should be understood that the attachment walls may extend around less than 50% of the external surface of the control knobs 130 and the handles 110. In such embodiments, the first and second connectors 10, 20 may be permanently or detachably attached to the handles 110 and the control knobs 130 using adhesives or the like.

The attachment portions 12, 14 of the first connector 10 may also include protrusions 15 that are shaped to engage features of the handle 110, for example, the raised ridges and valleys 114 shown in FIG. 2(a). In such embodiments, when the connector 10 is attached to the handle 110, the protrusions 15 nest in the valleys disposed between the raised ridges on the handle 110. In this configuration, when a longitudinal force is applied to the connector 10, the protrusions 15 and the ridges and valleys 114 engage each other and prevent relative movement, for example, sliding or the like, in the longitudinal direction between the first connector 10 and the handles 110. Similarly, the attachment portions 22, 24 of the second connector 20 may include protrusions 23 that engage portions of the control knobs 130. For example, the protrusions 23 may be configured to engage one or more ridges or lips 131 disposed on the surface of the control knobs 130. In this configuration, the protrusions 23 and the ridges 131 engage each other and prevent relative movement in the longitudinal direction between the second connector 20 and the control knobs 130.

FIG. 2(c) illustrates another embodiment of the first and second connectors 10' and 20', respectively. In this embodiment, the connector includes attachment portions 12, 14 that include horizontally extending walls shaped to engage the handles 110 and the control knobs 130, respectively, in a snap-fit arrangement. The first connector 10' may include a recessed portion 16 that is shaped to receive the ridges and valleys 114 of the handles 110, while the second connector 20' may include or one or more recessed portions 25 that are shaped to receive the ridges 131 of the control knobs 130. In this way, when the connector is subjected to longitudinal force, the recesses 16, 25 engage with the ridges 131 of the control knobs 130 and the proximal most and distal most ridges 114 on the handles 110, respectively. This interaction between the recesses 16, 25 and the ridges 131, 114 prevents relative movement in the longitudinal direction between the first connector 10' and the handles 110 and the second connector 20' and the control knobs 130.

As shown in FIGS. 3-7, in operation, initially two guidewires 2, 4 are advanced through a patient's vasculature to a bifurcated target site. For example, the target site may be, for example, a bilateral iliac atherosclerosis or the like disposed at a branched junction between the distal aorta or iliac bifurcation. Other exemplary target sites include the tibial bifurcation or trifurcation, the internal and external carotid artery, etc. The delivery systems 100 are advanced through the patient's vasculature over the guidewires 2, 4 to the target site. Once the delivery systems 100 have been advanced to a desired location for deployment of the stents 170, the first connector 10 is attached to the handles 110 and the second connector 20 is attached to the control knobs 130 of the of the delivery systems 100. The physician then releases the stents 170 by pulling either one of the handles 110 or the first connector 10 in the proximal direction toward the control knobs 130 while maintaining the control knobs 130 in a fixed position. Because the delivery systems 100 are connected by the first and second connectors 10, 20, the handles 110 move in unison, thereby simultaneously withdrawing the retention sheaths 140 of both delivery systems 100 in the proximal direction and simultaneously deploying the stents 170. As the retention sheaths 140 are withdrawn, the distal portions of the stents 170 expand in a radially outward direction against the respective branch vessels and the proximal portions of the stents 170 expand against each other to form a "kissing stent" configuration 30. By connecting the handles 110 and the control knobs 130 of the delivery systems 100, the first and second connectors 10, 20 may force the delivery systems to deploy their respective medical devices substantially simultaneously, thereby effectively eliminating the need for a second operator. Due to the simultaneous withdrawal of the sheaths 140, the connectors 10, 20 may also prevent the stents 170 from being misaligned during deployment.

Figure 8:
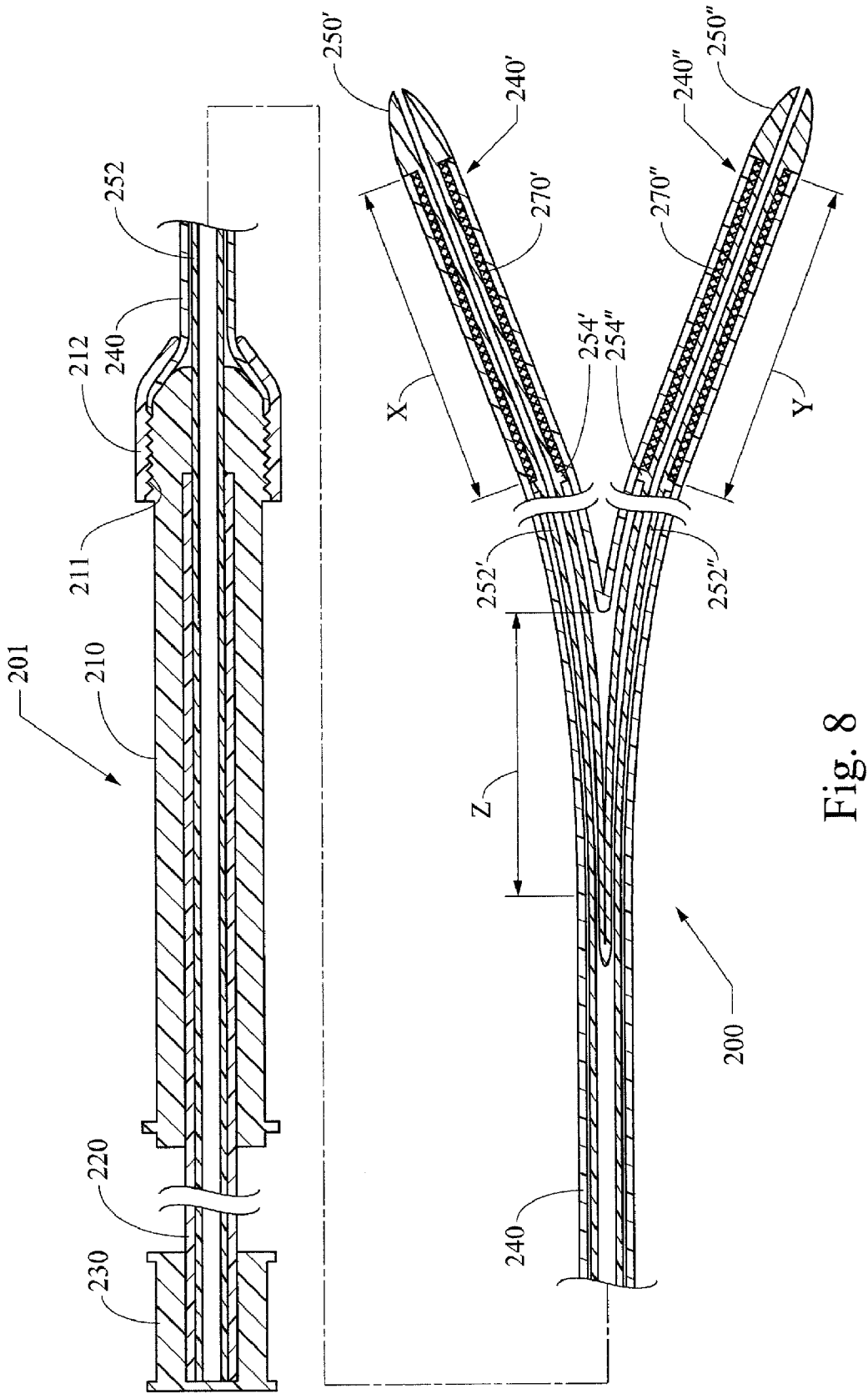
FIG. 8 is a side cross-sectional view of an embodiment of a simultaneous deployment delivery system.

Turning to FIG. 8, an embodiment of a simultaneous deployment delivery system 200 configured to deploy two or more medical devices simultaneously may include a Y-shaped retention sheath 240, a control device 201, and an inner catheter 252. The retention sheath 240 has a proximal portion with an outer diameter and an inner surface that defines an inner lumen extending axially along its length to a bifurcated distal portion of the sheath 240. The bifurcated distal portion includes first and second sheath branch portions 240', 240", each having proximal and distal ends. As shown in FIG. 8, the proximal ends of the branch portions 240', 240" are connected to each other and to the proximal portion of the sheath 240 to form a Y-shaped sheath branch junction. A proximal end of the proximal portion of the sheath 240 may be flared to a larger diameter and sealingly attached to a distal end of the handle 210 by sandwiching the flared portion between the handle 210 and a compression cap 212. The compression cap 212 may be releasably attached to the handle 210 by threads 211 or the like. The retention sheath 240 may be formed from a composite of different materials, with the base material being a lubricious material, for example PTFE (polytetrafluoroethylene) or the like. The retention sheath 240 also may incorporate wire coils or braids to increase the sheath's resistance to torsional and compressive forces.

The inner catheter 252 is disposed within the bifurcated sheath 240 and, like the sheath 240, may have a proximal portion formed from a single tube-like structure and a distal bifurcated portion. In one embodiment, the proximal portion includes a single lumen extending along its length to accommodate, for example, both guidewires 2, 4 shown in FIGS. 9-11. In another embodiment, the proximal portion may comprise two or more lumens to accommodate the guidewires 2, 4. In yet another embodiment, the delivery system 200 may be configured as a rapid exchange catheter and may include insertion ports disposed at or near a distal end of the proximal portion of the sheath 240 and the inner catheter 252 that are configured to receive the guidewires 2, 4.

Returning to FIG. 8, the distal bifurcated portion of the inner catheter 252 includes two catheter branch portions 252', 252", which are disposed coaxially within the sheath branch portions 240', 240". The catheter branch portions 252', 252" each have proximal and distal ends, with the proximal ends of the branch portions 252', 252" being connected to each other, and to the proximal portion of the inner catheter 252 to form a Y-shaped catheter branch junction. Each of the branch portions 252', 252" may include a stop 254', 254", respectively, that extends radially outward from the branch portions of the inner catheter 252', 252" and a distal tip 250 that may be bonded to the distal ends of the branch portions 252', 252" using an adhesive or the like. A distal surface of the stops 254', 254" is located adjacent the proximal end of the medical devices 270', 270", which are disposed on the catheter branch portions 252', 252" and housed within the sheath branch portions 240', 240", respectively. In an alternative embodiment, the inner catheter 240 may include two catheter tubes that are separated at a distal portion thereof to form the catheter branch portions 240', 240" and coupled together in the proximal portion to form the catheter branch junction.

The inner catheter 252 may extend through the handle 210, a shaft 220, and a control knob 230 of the control device 201. Alternatively, the proximal end of the inner catheter 252 may be sealingly connected to the shaft 220. At least a distal portion of the shaft 220 is slidably disposed within the handle 210 while a proximal portion of the shaft 220 is fixedly attached to the control knob 230.

As with the embodiment shown in FIGS. 1-7, the medical devices 270', 270" may be self-expanding stents or the like that are released from the delivery system by withdrawing the retention sheath 240 proximally relative to the inner catheter 252, as described above in connection with the embodiment of FIGS. 1-7. The medical device 270' may have a length X, while the medical device 270" may have a length Y. In some embodiments, the length X may be the same as the length. In other embodiments, the length X may be greater than the length Y, or vice versa, in order to accommodate lesions having dissimilar lengths in different branches of the vessel.

As shown in FIG. 8, once assembled in the initial, pre-deployment state, the junction between the catheter branch portions 252', 252" is displaced proximally from the junction between the sheath branch portions 240', 240" by a distance Z. The distance Z has a minimal length that is equal to the longer of the lengths X and Y of the medical devices 270', 270" to allow the sheath to be withdrawn a sufficient amount to release the medical devices 270', 270". For example, if the medical device 270' is a stent having a length of 40 mm, and the medical device 270" is a stent having a length of 35 mm, the distance Z the sheath branch junction is displaced from the catheter branch junction is at least 40 mm. However, it should be understood that the distance Z may be greater than the length of longer of the medical devices 270', 270" to accommodate, for example, sheath elongation or sheaths that extend beyond the distal end of the medical devices 270', 270". By displacing the catheter branch junction proximally from the sheath branch junction, it is possible to utilize a sheath 240 that completely surrounds and restrains the medical devices 270', 270" and that can accommodate a composite structure including wire braids or coils to improve the ability to advance and torque the delivery system 200 through tortuous anatomy without compromise. That is, there is no need to employ so-called "tear away sheaths" or sheaths that can be disassembled using complicated release mechanisms in order to remove the sheath 240 and deploy the medical devices 270', 270" housed therein.

Figure 9:
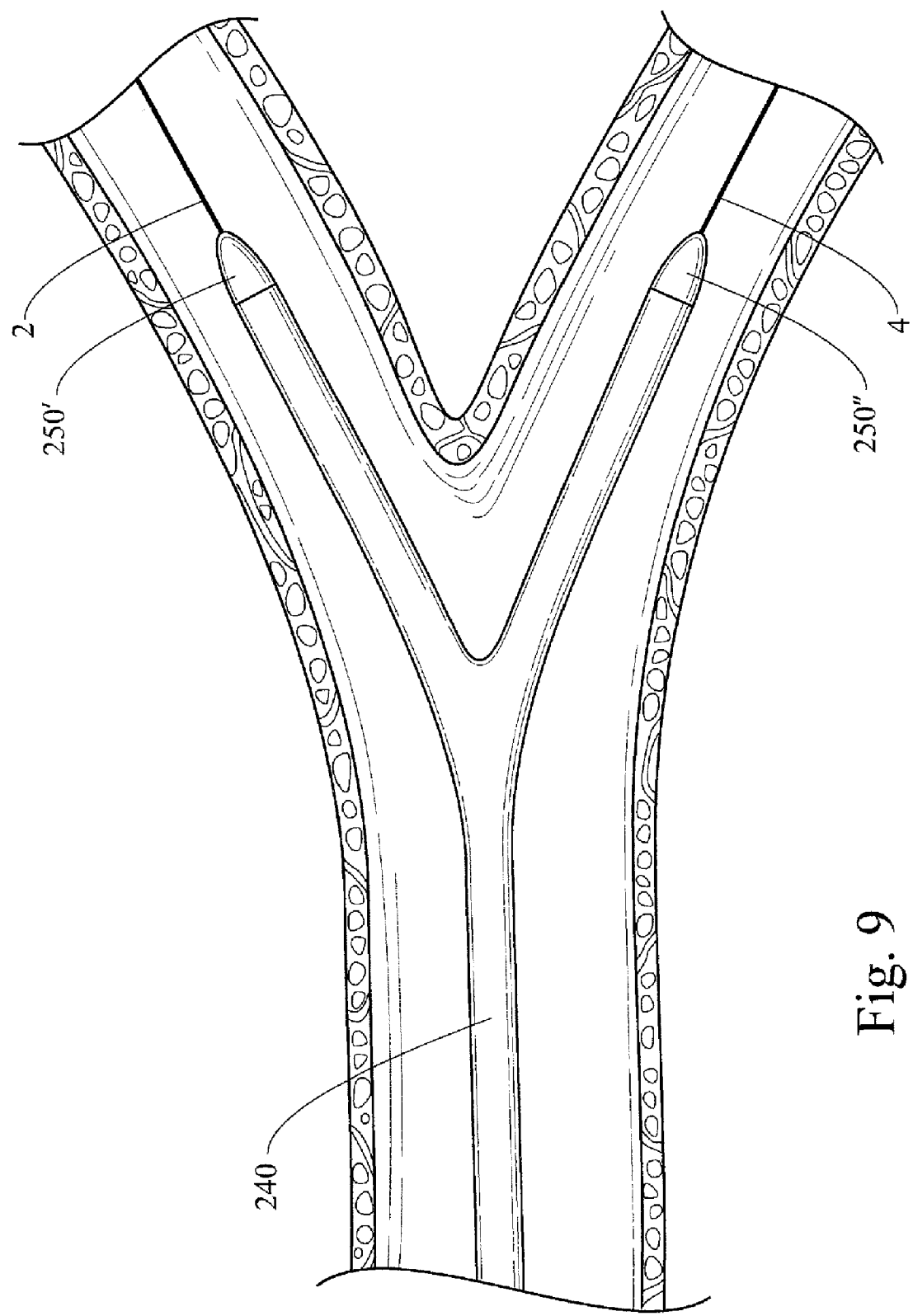
FIGS. 9-11 illustrate a deployment process for the medical devices housed within the simultaneous deployment delivery system of FIG. 8.
Figure 10:
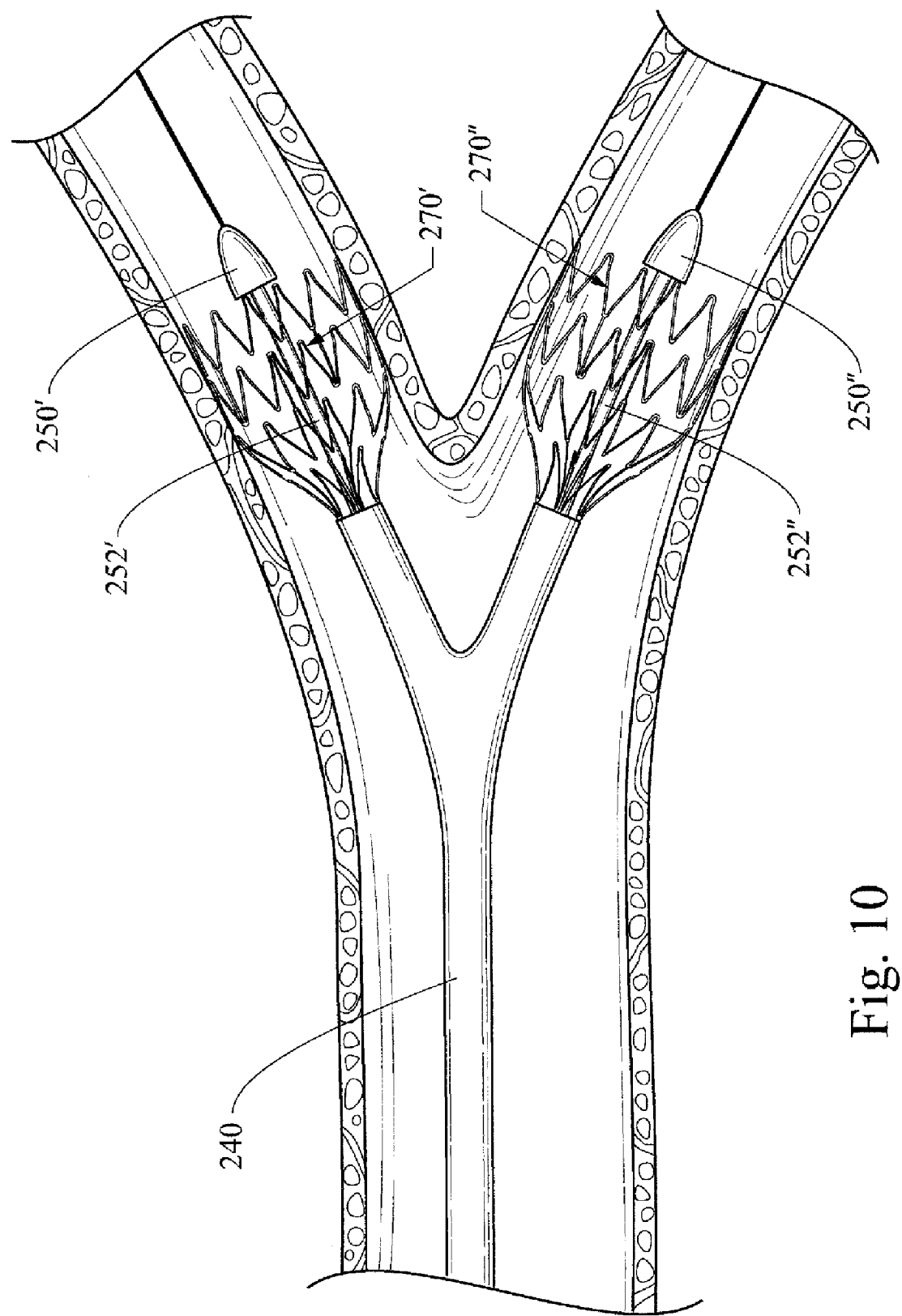
Figure 11:
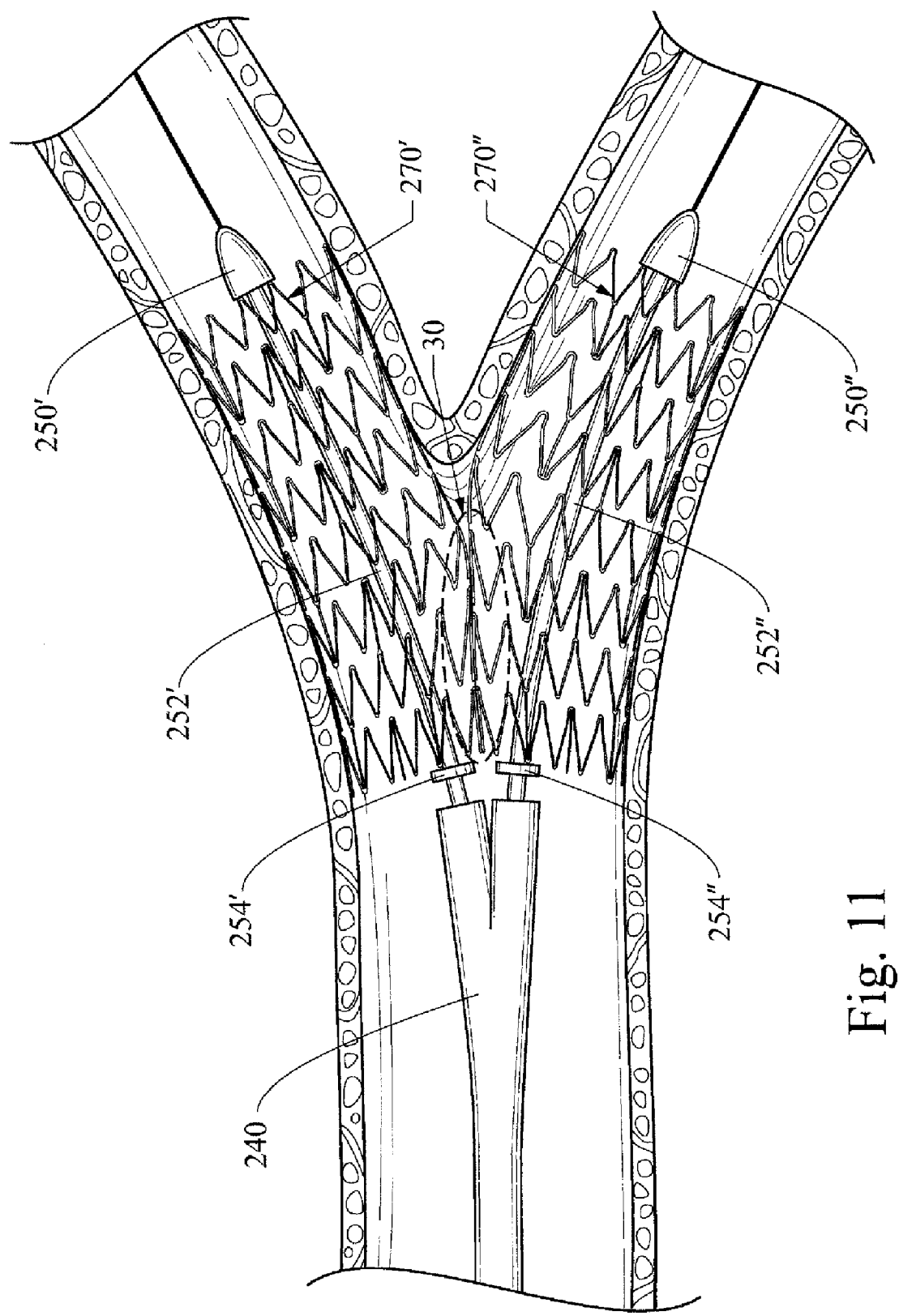

As shown in FIGS. 9-11, in operation, initially two guidewires 2, 4 are advanced through a patient's vasculature and the delivery system 200 is advanced over the guidewires 2, 4 to the bifurcated target site. Once the catheter and sheath branch portions 240', 252', 240", 252" have been advanced to a desired location for deployment of the medical devices 270', 270", the physician then releases the medical devices 270', 270" by pulling the handle 210 toward the control knob 230 while maintaining the control knob 230 in a fixed position. As the handle 210 is withdrawn proximally to the deployment position, the sheath branch portions 240', 240" are withdrawn simultaneously over the medical devices 270', 270", thereby allowing the distal portions of the medical devices 270', 270" expand in a radially outward direction against the respective branch vessels. As the handle continues to be withdrawn, the proximal portions of the medical devices 270', 270" simultaneously expand against each other to form a "kissing stent" configuration 30.

Figure 12A:
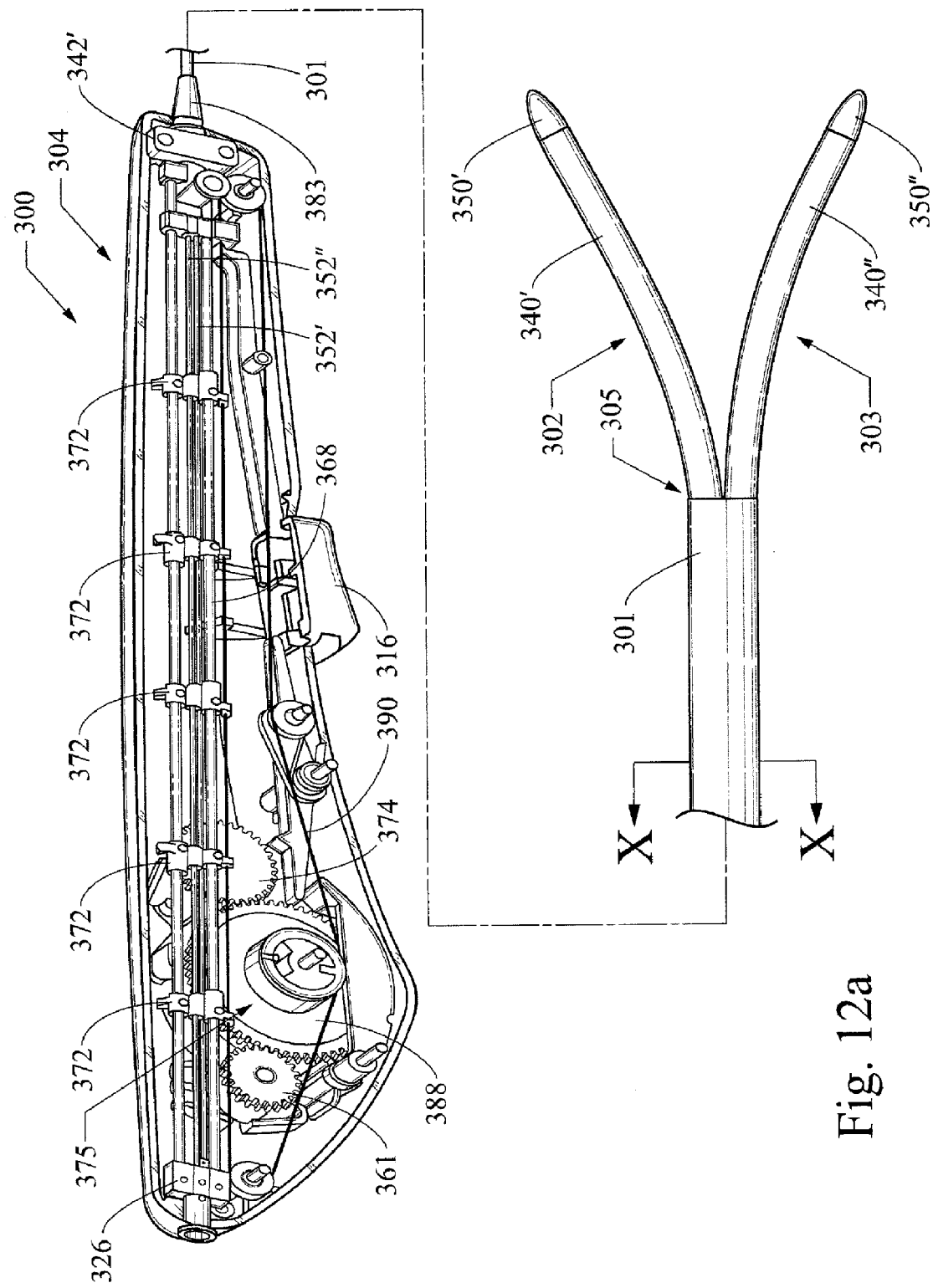
FIG. 12(a) is a partial cross-sectional view of a control device of another embodiment of the simultaneous deployment system.
Figure 12B:
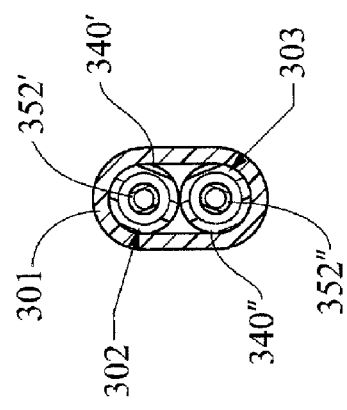
FIG. 12(b) is a cross sectional view of a catheter assembly taken along the line X-X of FIG. 12(a)
Figure 12C:
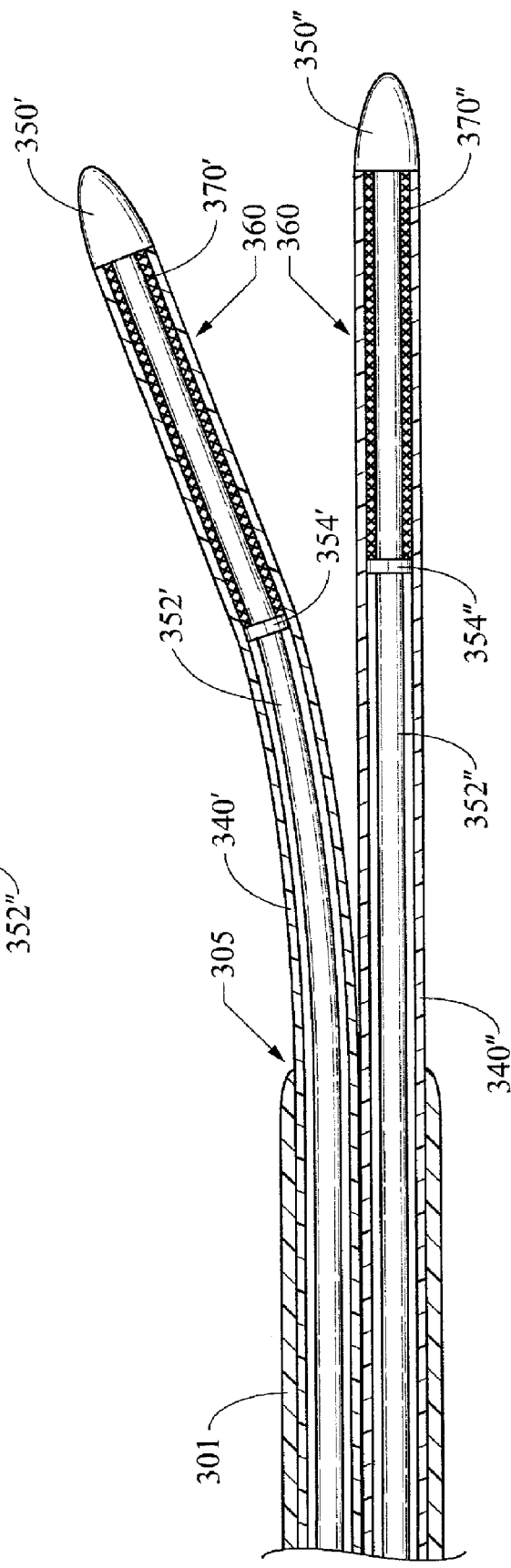
FIG. 12(c) is a partial cross-sectional view of a distal portion of the delivery system of FIG. 12(a)
Figure 13:
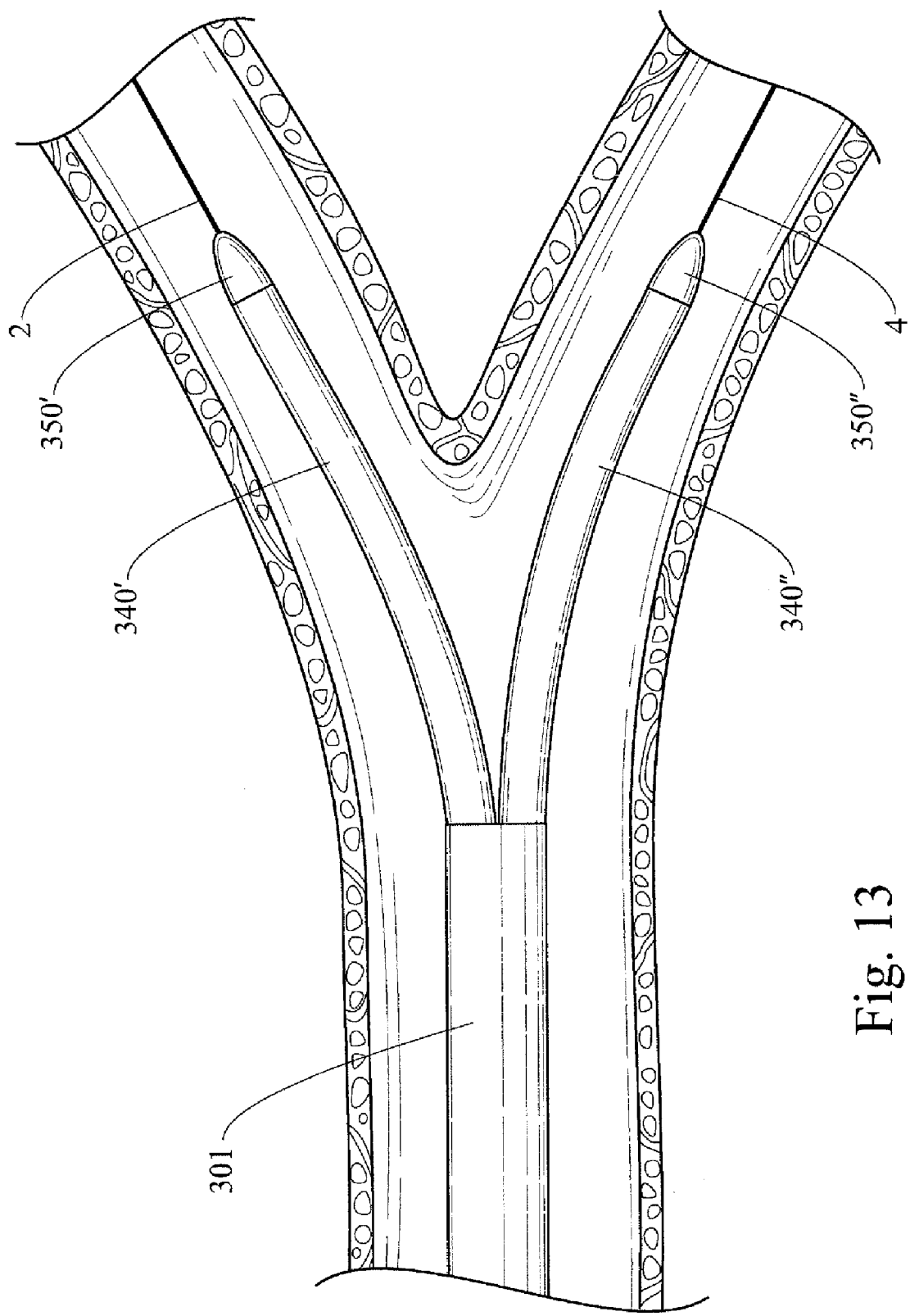
FIGS. 13-15 illustrate a deployment process for the medical devices housed within the simultaneous deployment delivery system of FIGS. 12(a)-(c).

FIGS. 12(a)-(c) illustrate another embodiment of a deployment delivery system 300 configured to deploy two or more medical devices simultaneously. As shown in FIGS. 12(a)-(c), the delivery system 300 may include an outer sheath 301 disposed around first and second catheter assemblies 302, 303, and a control device 304. Each of the catheter assemblies 302, 303 includes a retention sheath 340', 340" having an outer diameter and an inner surface that defines an inner lumen extending axially along its length. The outer sheath 301 and the retention sheaths 340', 340" may be formed from a composite of different materials, with the base material being a lubricious material, for example PTFE (polytetrafluoroethylene) or the like. The outer sheath 301 and the retention sheaths 340', 340" also may incorporate wire coils or braids to increase the sheath's resistance to torsional and compressive forces and improve manipulation and pushability as the delivery system 300 is advanced through tortuous anatomy.

An inner catheter 352', 352" is disposed within each of the retention sheaths 340', 340", as shown in FIG. 12(c). Each inner catheter includes a guidewire lumen disposed therein and a device containing region 360 disposed at a distal end thereof. The device containing region 360 is bounded by one end by a stop 354', 354" at a proximal end and a distal tip 350', 350" at a distal end. A medical device 370', 370", for example, a self-expanding stent or the like, is housed in the device containing region 360 in a collapsed or compressed configuration and is covered by the retention sheaths 340', 340", respectively. As shown in FIG. 12(b), the outer sheath 301 is sized such that a cross sectional area at any given longitudinal point along its length is substantially the same as the cross sectional areas of the retention sheaths 340', 340" of the catheter assemblies 302, 303. That is, as shown in FIG. 12(b), the outer sheath 301 is sized such that any gaps between the catheter assemblies 302, 303 and the outer sheath 301 are minimized to minimize package size and support the retention sheaths 340', 340". The outer sheath 301 extends distally from the control device 304 to a diverging point 305 between the catheter assemblies 302, 302 that is disposed at least proximal of the stop 354', 354" in order to allow the device containing regions 360 to be inserted into the diverging branch vessels for deployment of the medical devices 370', 370". In one embodiment, the catheter assemblies 302, 303 may be configured as a rapid exchange catheters and may include insertion ports disposed at or near the distal end of the outer sheath 301. Because the outer sheath 301 extends along the majority of the length of the catheter assemblies 302, 303, the outer sheath 301 helps support the catheter assemblies and improves pushability as they are advanced through tortuous anatomy to the treatment site.

The control device 304 may be an automated retraction handle as disclosed in U.S. patent application Ser. No. 12/459,577, entitled "Deployment Assembly and Introducer," which is assigned to Cook, Inc. the assignee of the present application, the entirety of which is hereby incorporated herein by reference. As shown in FIG. 12(a), a proximal end of the outer sheath 301 may be fixedly attached to a distal end of the control device 304 by a tip 383. A proximal end of the retention sheaths 340', 340" may be fixedly attached to a glider member 342 that is slidably mounted on a pair of support cannulas 368. One cannula 368 may be disposed near an upper end of the glider 342 and one cannula 368 may be disposed near a lower end of the glider 342. A drive cable 390 is attached to the glider 342 and connected to a drive motor 375 through a series of pulleys and guides. The inner catheters 352', 352" extend through the tip 383, the glider 342, and through a length of a housing of the control device 304. The proximal ends of the inner catheters 352', 352" are attached to an anchor 326 disposed at a proximal end of the housing. The inner catheters 352', 352" are supported along the portion disposed within the housing by a plurality of sliding supports 372 disposed on the support cannulas 368.

Figure 14:
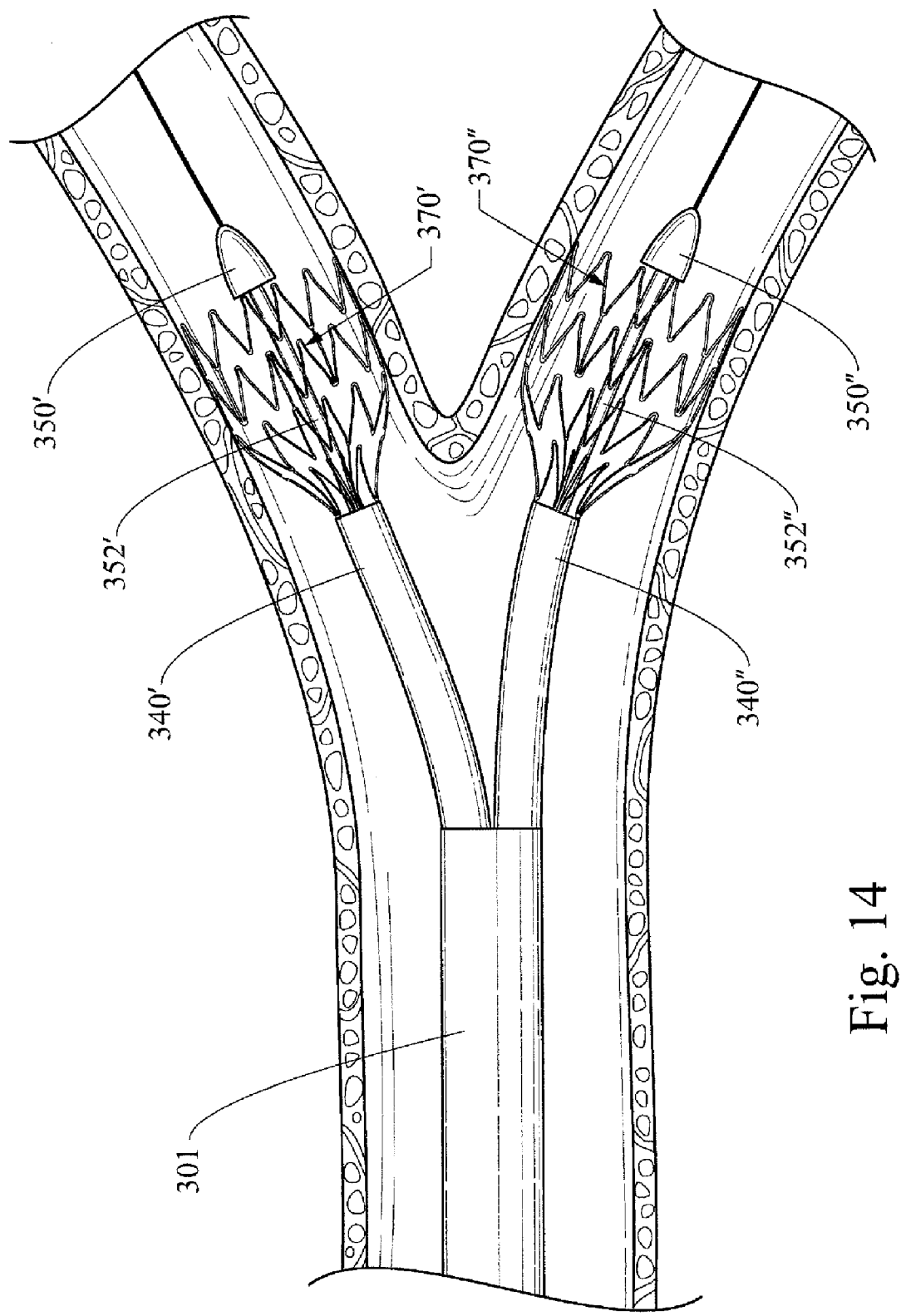
Figure 15:
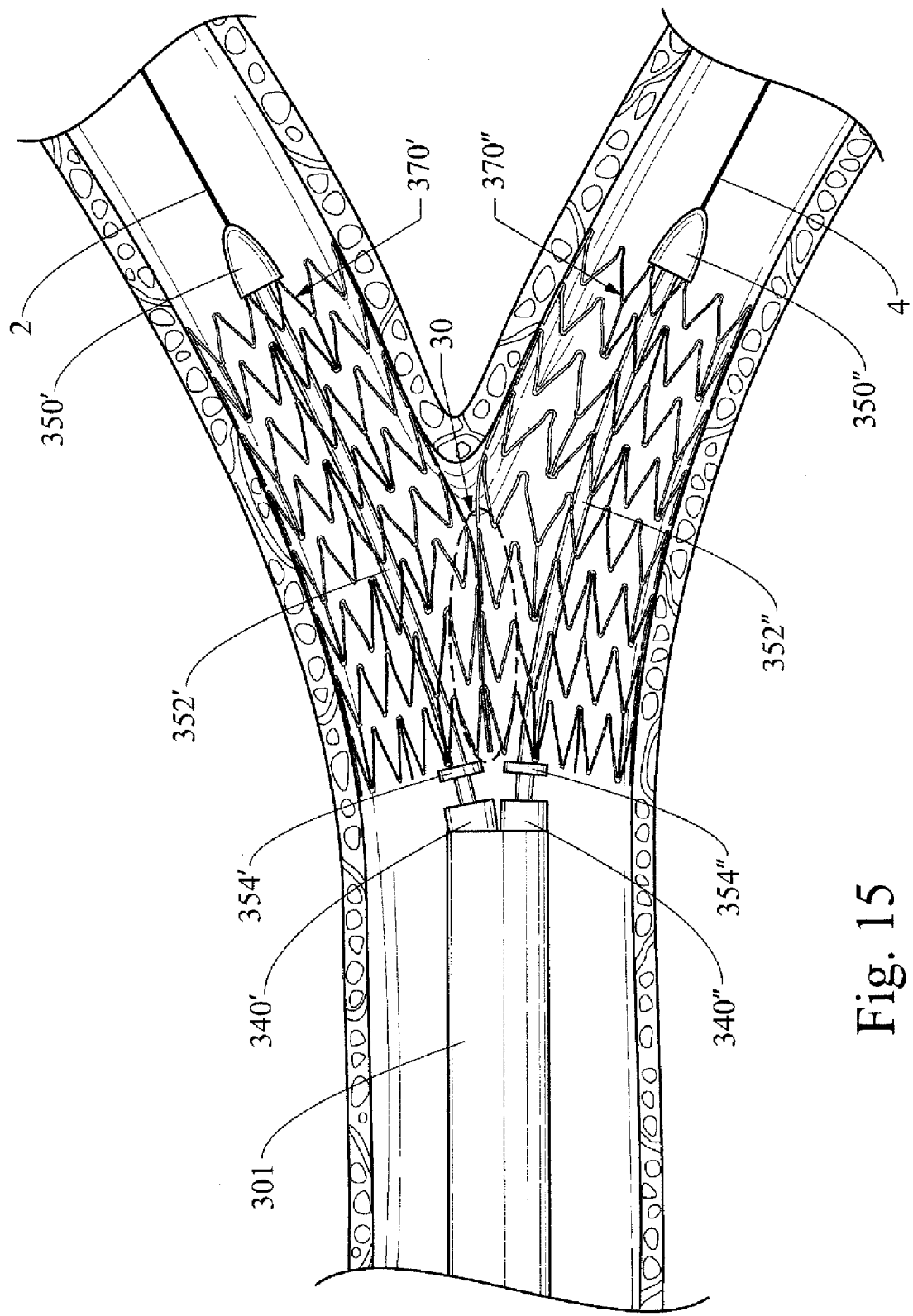

In operation, initially, two guidewires 2, 4 are advanced through a patient's vasculature and the delivery system 300 is advanced over the guidewires 2, 4 to the bifurcated target site. Once the catheter assemblies 302, 303 have been advanced to a desired location for deployment of the medical devices 370', 370," a trigger 316 is actuated by an operator, which initiates the drive motor 375 by releasing a pre-wound torsion spring attached to a drive gear 388. As the drive gear 388 turns, it is damped by gears 361 and 374, which are attached to fluid damper units that control the speed at which the drive gear 388 rotates. As the drive gear 388 turns, the drive cable 390 is pulled in a counter clockwise direction and wound around a spool attached to the drive gear 388. The counter clockwise movement of the drive cable 390 pulls the glider member 342 in the proximal direction along the cannulas 368, which act as a track for the glider member 342. As shown in FIGS. 14 and 15, as the glider member 342 is withdrawn proximally by the drive cable 390, the retention sheaths 340', 340" are simultaneously withdrawn in the proximal direction through the stationary outer sheath 301. Because the outer sheath 301 is held stationary and the retention sheaths 340', 340" are withdrawn through the outer sheath 301, the outer sheath 301 prevents contact between and shields the vessel wall from all but the distal portion of the retention sheaths 340', 340". This shielding of the vessel wall may help reduce damage or irritation to the patient's vasculature caused by sliding friction of the retention sheaths 340', 340" as they are withdrawn to deploy the medical devices 370', 370". Further, because the outer sheath 301 supports the retention sheaths 340', 340", the outer sheath 301 may improve the accuracy of placement of the medical devices 370', 370" by reducing any tendency of the catheter assemblies 302, 303 to buckle or compress under the withdrawal/deployment forces.

As the sheaths 340', 340" continue to be withdrawn the distal portions of the medical devices 370', 370" expand in a radially outward direction against the respective branch vessels until the proximal portions of the medical devices 370', 370" simultaneously expand against each other to form a "kissing stent" configuration 30.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A medical device delivery system, comprising:
an outer sheath connected to a first portion of a handle;
first and second inner catheters attached to a second portion of said handle;
a first retention sheath disposed around said first inner catheter and connected to a third portion of said handle;
a second retention sheath disposed around said second inner catheter and connected to said third portion of said handle;
a first medical device disposed around said first inner catheter and within said first retention sheath;
a second medical device disposed around said second inner catheter and within said second retention sheath;
wherein said first and second retention sheaths are slidably disposed within a central lumen of said outer sheath, and wherein said third portion of said handle is movable relative to said first and second portions of said handle between a first position, and a second position, wherein said first and second medical devices are deployed simultaneously when said third portion of said handle is moved to said second position.

2. The medical device of claim 1, wherein a distal portion of said first and second inner catheters are free from attachment to each other and a distal portion of said retention sheaths are free from attachment to each other, said distal portions of said first and second inner catheters and retention sheaths extending distally beyond a distal end of said outer sheath, and wherein, in said first position, said first and second retention sheaths are disposed around and restrain said first and second medical devices, respectively, and in said second position, said first and second retention sheaths are withdrawn proximally to deploy said first and second medical devices.

3. The medical device of claim 2, wherein said first and second medical devices are disposed in a device containing region of said first and second inner catheters, said device containing region being disposed distally of a distal end of said outer sheath.

4. The medical device of claim 3, wherein said first and second medical devices are self-expanding stents and an entirety of said device containing regions are displaced from said distal end of said outer sheath by substantially the same distance.

5. The medical device of claim 2, wherein said first portion and said outer sheath remains stationary relative to said second portion and said first and second inner catheters when said third portion of said handle is moved between said first and second positions.

6. The medical device of claim 2, wherein a cross-sectional area of said outer sheath is substantially equal to a combined cross-sectional area of said first and second retaining sheaths.

* * * * *